(12) United States Patent
Gara et al.

(10) Patent No.: US 10,227,269 B2
(45) Date of Patent: Mar. 12, 2019

(54) CYCLOPROPANATION OF SUBSTITUTED ALKENES

(71) Applicant: International Flavors & Fragrances Inc., New York, NY (US)

(72) Inventors: Mohamad Gara, Jatt Village (IL); Yigal Becker, Tel-Aviv (IL)

(73) Assignee: International Flavors & Fragances Inc., New York, NY (US)

( * ) Notice: Subject to any disclaimer, the term of this patent is extended or adjusted under 35 U.S.C. 154(b) by 0 days.

(21) Appl. No.: 15/735,712

(22) PCT Filed: Aug. 4, 2016

(86) PCT No.: PCT/US2016/045540
§ 371 (c)(1),
(2) Date: Dec. 12, 2017

(87) PCT Pub. No.: WO2017/024126
PCT Pub. Date: Feb. 9, 2017

(65) Prior Publication Data
US 2018/0170830 A1 Jun. 21, 2018

Related U.S. Application Data

(60) Provisional application No. 62/201,720, filed on Aug. 6, 2015.

(51) Int. Cl.
| | |
|---|---|
| *C07C 2/00* | (2006.01) |
| *C11B 9/00* | (2006.01) |
| *B01J 23/00* | (2006.01) |
| *C07C 2/86* | (2006.01) |
| *C07C 29/32* | (2006.01) |
| *C07C 45/69* | (2006.01) |
| *A23L 27/20* | (2016.01) |
| *B01J 23/06* | (2006.01) |
| *B01J 23/72* | (2006.01) |
| *B01J 35/00* | (2006.01) |
| *B01J 35/02* | (2006.01) |
| *C07C 29/44* | (2006.01) |
| *C07C 45/61* | (2006.01) |

(52) U.S. Cl.
CPC ............ *C07C 2/861* (2013.01); *A23L 27/203* (2016.08); *B01J 23/06* (2013.01); *B01J 23/72* (2013.01); *B01J 35/0006* (2013.01); *B01J 35/026* (2013.01); *C07C 29/32* (2013.01); *C07C 29/44* (2013.01); *C07C 45/61* (2013.01); *C07C 45/69* (2013.01); *C11B 9/00* (2013.01); *C11B 9/003* (2013.01); *C11B 9/0026* (2013.01); *C11B 9/0042* (2013.01); *C11B 9/0049* (2013.01); *C11B 9/0057* (2013.01); *C07C 2523/06* (2013.01); *C07C 2523/72* (2013.01); *C07C 2601/02* (2017.05); *C07C 2601/08* (2017.05); *C07C 2601/10* (2017.05); *C07C 2602/18* (2017.05); *C07C 2602/20* (2017.05); *C07C 2602/32* (2017.05); *C07C 2602/40* (2017.05); *C07C 2602/50* (2017.05); *C07C 2603/08* (2017.05); *C07C 2603/62* (2017.05); *C07C 2603/96* (2017.05)

(58) Field of Classification Search
CPC . C07C 2/861; C11B 9/103; B01J 23/06; B01J 23/72
See application file for complete search history.

(56) References Cited

U.S. PATENT DOCUMENTS 5,929,291 A * 7/1999 Bajgrowicz ............ C07C 31/13
512/19

OTHER PUBLICATIONS

Takai et al. A Dramatic Effect of a Catalytic Amount of Lead on the Simmons-Smith Reaction and Formation of Alkylzinc Compounds from Iodoalkanes. Reactivity of Zinc Metal: Activation and Deactivation. Journal of Organic Chemistry, vol. 59, 2671-2673. (Year: 1994).*

LeGoff. Cyclopropanes from and Easily Prepared, Highly Active Zinc-Copper Couple, Dibromomethane, and Olefins. Journal of Organic Chemistry, vol. 29, 2048-2050. (Year: 1964).*

* cited by examiner

*Primary Examiner* — Sikarl A Witherspoon
(74) *Attorney, Agent, or Firm* — Martin Zhang; XuFan Tseng; Elizabeth M. Stover

(57) ABSTRACT

Disclosed is a cyclopropanation process comprising the step of reacting an alkene compound having at least one carbon-carbon double bond with at least one dihaloalkane. The reaction is carried out in the presence of (i) particulate metal Zn, (ii) catalytically effective amount of particulate metal Cu or a salt thereof, (iii) at least one haloalkylsilane, and (iv) at least one solvent.

11 Claims, No Drawings

CYCLOPROPANATION OF SUBSTITUTED ALKENES

CROSS REFERENCE TO RELATED APPLICATIONS

This application is a national stage entry under 35 USC 371 for International Application No. PCT/US2016/045540, filed on Aug. 4, 2016. The international application claims priority to U.S. Application No. 62/201,720, filed on Aug. 6, 2015. The contents of both applications are incorporated herein by reference in their entirety.

TECHNOLOGICAL FIELD

The present application provides processes for cyclopropanation of substituted alkenes using dihalomethane having improved conditions and yields.

BACKGROUND

Simmons and Smith reported in 1958 the first cyclopropanation of alkenes using methylene iodide and zinc-copper couple in ether (*Organic Reactions*, vol. 20, 1, 1973). The reactive carbenoide was inferred to be iodomethylzinc iodide ($ICH_2ZnI$) in Schlenc equilibrium with $Zn(CH_2I)_2$ and $ZnI_2$. The reaction was found to be stereospecific namely the configuration of the olefin was retained in the product. The reaction required very long times (16-72 hours) and yields varied from 7% to 70%.

Ethylene was steadily generated during the reaction by dimerization of methylene iodide, its amount was inversely proportional to the amount of the cyclopropanation product. Chloroiodomethane reacted poorly and dibromomethane (DBM) was found unreactive (Simmons and Smith, *J. Am. Chem. Soc.*, 81(16), 4256, 1959). The zinc-copper couple was prepared by melting zinc and copper powder followed by crushing the solid. Later researches simplified the procedure by in-situ treatment of granular zinc or zinc dust with copper or silver salts in acetic acid (Charette and Beauchemin, *Organic Reactions*, 58, chapter 1, pp. 1-415, 2001).

In view of the importance of the Simmons-Smith cyclopropanation as synthetic tool, continuous efforts were made to replace the expensive methylene iodide by the much cheaper DBM and new conditions were sought to increase the reaction rate.

LeGoff (*J. Org. Chem.*, 29(7), 2048, 1964) found that increased activation of granular zinc was achieved by addition of $Cu(OAc)_2 \cdot H_2O$ in acetic acid. This couple allowed the use of DBM in the cyclopropanation of cyclohexene and cyclooctene in diethyl ether. The reaction times were 25-40 hours and the yields were 61% and 40% respectively. The yields were much lower than with methylene iodide and were not reproducible. Zinc dust-copper couple gave much lower yields.

Fabisch and Mitchell cyclopropanated simple olefins with DBM and zinc in tetrahydrofuran (THF) as a solvent. See *J. Organometal. Chem.*, 269(3), 219, 1984. The reactions were carried out at 40° C. for 48 hours in absence of copper. The yields varied from 35% to 52.8%. Ethylene formation was observed. NMR analysis in perdeuterated THF was consistent with $BrZnCH_2Br$. NMR showed that on standing $BrZnCH_2Br$ was converted to $Zn(CH_2Br)_2$ and $ZnBr_2$.

Friedrich, Domek, and Pong improved significantly the DBM cyclopropanation of simple olefins by sonication of zinc dust in presence of 10 mol % CuCl in refluxing ether. See *J. Org. Chem.*, 50(23), 464, 1985. After an induction period (0.5-1 hr) the reaction commenced and was over in 2-4 hours. The yields varied from 28-50%, where cyclohexene and cyclooctene gave 60% and 72% yield respectively.

These reaction conditions were applied to the synthesis of odorant II according to U.S. Pat. No. 5,929,291 (Bajgrowicz and Frater, 1999, Givaudan Roure Int).

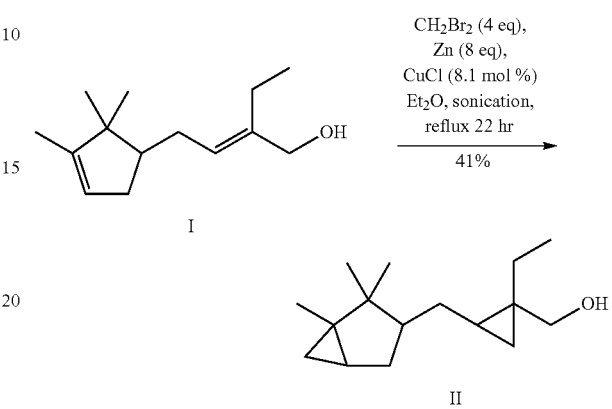

The biscyclopropanated product II was obtained from the allylic alcohol I in 41% yield after continued sonication for 22 hours. To eliminate the induction period the reaction mixture containing DBM, zinc powder, and cuprous chloride in ether was sonicated for 30 minutes prior to the addition of I. The product exhibited sandalwood, fruity, creamy/milk-like, very long-lasting odor.

Friedrich, Lunetta, and Lewis reported (*J. Org. Chem.*, 54(10), 2388, 1989) that sonication was not necessary when the zinc-copper couple was promoted by titanium tetrachloride (1.5-2 mole %). The reaction times were less than 2 hours and the yields were comparable to sonication. DBM and methylene iodide gave similar yields.

Friedrich and Lewis (*J. Org. Chem.*, 55(8), 2491, 1990) found that the effect of addition of 2 mole % of acetyl chloride to zinc-copper couple is even stronger than titanium tetrachloride. Cyclopropanation of unactivated alkenes with DBM in refluxing ether in presence of 10 mole % copper chloride required 1-2 hours for completion. The yields varied from 33% to 76%. Cyclohexene and cyclooctene gave 61% and 88% yield respectively. Trimethylsillyl chloride was claimed to have similar promoting effect but no example was given.

The main disadvantage of Frederich procedures is the use of diethyl ether, an extremely flammable solvent (flash point of −45° C.) which could be explosive. Diethyl ether vapor is heavier than air thus accumulates and travels on ground and may be ignited by hot surfaces, static electricity or other ignition sources. Being sensitive to light and air it tends to form explosive peroxides. Taking account of its low boiling point (34.6° C.) and anesthetic properties its handling in production site requires very efficient heat exchangers to completely eliminate its release to the environment.

Zinc promoters such as chlorotrimethylsilane were later demonstrated to suppress the retarding effect of traces of lead in commercial zinc powder. Takai, Kakiuchi, and Utimoto. (*J. Org. Chem.*, 59(10), 2671, 1994) demonstrated that a trace amount of lead found in pyrometallurgic zinc decreases the reactivity of zinc toward diiodomethane and iodoalkanes substantially, and this negative effect can be completely suppressed by the addition of a catalytic amount of $Me_3SiCl$.

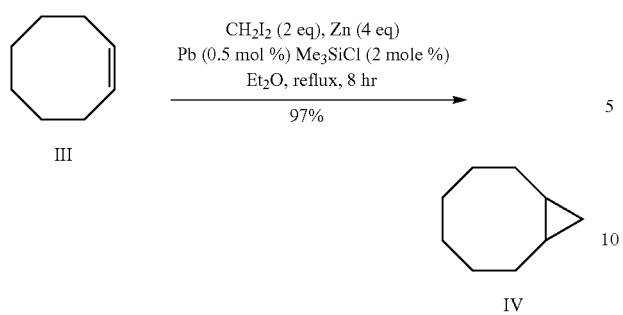

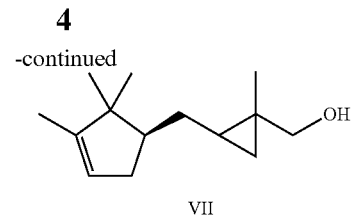

Thus, when methylene iodide was reacted with cycloctene (III) and lead-free (electrolytic) zinc dust in boiling ether for 8 hours, IV was obtained in 96% yield. NMR showed the presence of the carbenoid $ICH_2ZnI$. However, when zinc dust containing 0.06 mole % of lead was used, the yield dropped to 2%, and no $ICH_2ZnI$ was detected. The addition of trimethylsilyl chloride (2 mole %) to zinc dust containing 0.5 mole % lead gave IV in 97% yield.

The promoted Friedrich cyclopropanation was applied to (E)-2-methyl-4-(2,2,3-trimethylcyclopent-3-enyl)but-2-en-1-ol (V) for the synthesis of [1-methyl-2-(1,2,2-trimethyl-bicyclo[3.1.0]hex-3-ylmethyl)cyclopropyl]methanol (VI, Javanol™), a fragrance ingredient. See U.S. Pat. No. 5,929,291.

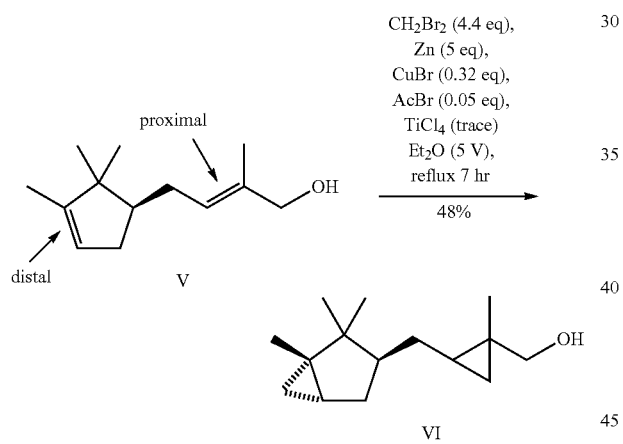

Javanol™ was prepared in 48% yield. It exhibited sandalwood, very natural, floral, creamy, powdery, very strong and long-lasting odor.

The DBM-zinc cyclopropanation of V was shown (Bajgrowicz, Frank, and Frater, *Helv. Chim. Acta,* 81(7), 1349, 1998) to proceed in two steps, the faster step was the proximal cyclopropanation affording VII which was isolated in mere 14% yield. VII exhibits creamy, lactonic sandalwood odor.

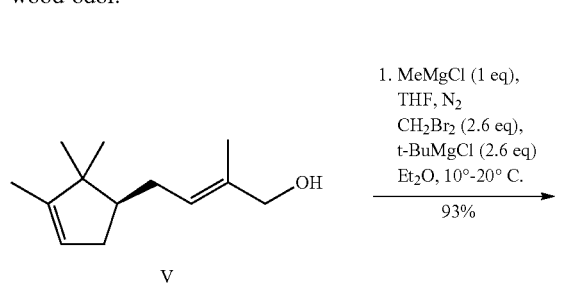

The monocyclopropanated alcohol VII was later prepared by improved method based on magnesium carbenoid in 93% yield. Deprotonation of V with methylmagnesium chloride in THF was followed by reaction with DBM and tert-butylmagnesium chloride in diethyl ether at 10-20° C. See U.S. Pat. No. 8,450,533. Involvement of the magnesium carbenoid $XMgCH_2X$ as the active cyclopropanation agent was proposed (Brunner et al, *J. Org. Chem.* 73(19), 7543, 2008).

Javanol™ was also prepared by two consecutive cyclopropanations with DBM as solvent in high overall yield. U.S. Pat. No. 7,777,084 showed that triisobutyl-aluminium-$FeCl_3$ catalyzed the distal cyclopropanation of V in presence of large excess of DBM as solvent at room temperature in 4 hours to afford VIII in quantitative yield. Aluminum carbenoid $(iBu)_2AlCH_2Br$ was detected by NMR. After work-up, azeotropic drying and concentration of DBM down to 3 equivalents per 1 equivalent VIII, the magnesium carbenoid proximal cyclopropanation was applied to afford VI in 82% yield. See Brunner, Elmer, and Schroder, *Eur. J. Org. Chem.,* 24, 4623, 2011.

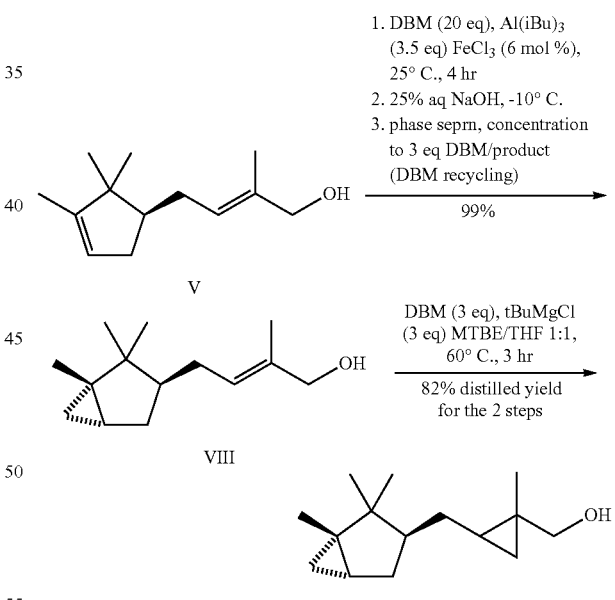

The reactions exhibit high stereospecificity and high overall yields. Although DBM was used in very large excess it is recyclable. Unlike the previous methods the aqueous waste was free of zinc and copper salts. The disadvantages are the use of large excess of DBM of relatively low reactivity and large excess of expensive and pyrophoric triisobutylaluminum and t-Butyl magnesium chloride. The first step reactor throughput is only 4.3%. The aqueous waste contains large amounts of aluminum and magnesium hydroxides.

Rieke et al, (*J. Org. Chem.*, 46(21), 4323, 1981) prepared highly active form of nanozinc by reducing zinc chloride with lithium in boiling dimethoxyethane. After exchanging the solvent with diethyl ether, cyclohexene was cyclopropanated with DBM by reflux for 6 hours to give bicyclo [4.1.0]heptane in 94% yield. The use of the highly corrosive lithium metal and its high sensitivity to water combined with the required solvent exchange to diethyl ether renders this method less attractive on industrial scale.

Sibille et al, (*J. Org. Chem.*, 56(10), 3255, 1991) described the electrochemical cyclopropanation of allylic alcohols with DBM using zinc rod anode and carbon fiber cathode. The electrolysis was performed in a mixture of dichloromethane (DCM) and dimethylformamide (DMF) containing a mixture of $Bu_4NBr/Bu_4NI$ and $ZnBr_2$ generated by pre-electrolysis of 1,2-dibromoethane. The yields varied from 52% to 75%. Bromochloromethane (CBM) was used in the cyclopropanation of E-crotyl alcohol, E-cinamyl alcohol and 2-cyclohexen-1-ol in 54%, 59% and 75% yield respectively. Although cyclopropanation with the cheaper CBM was demonstrated for the first time, the need for dedicated electrochemical device capable of controlling the reaction heat greatly limits its application on industrial scale.

In spite of the research and development of the Simmons-Smith cyclopropanation process over the past 57 years, there is still a need for economic, rapid and safe cyclopropanation of alkenes in high yield.

GENERAL DESCRIPTION

The present invention describes the first practical use of a dihaloalkane, such as bromochloromethane (CBM), in a process for cyclopropanation of an alkene. It was surprisingly found by the inventors of the present application that dihaloalkanes as methylene source (such as CBM) provide high yield and very rapid cyclopropanation process of substituted alkenes. The process is characterized by high selectivity and higher reactor throughput compared to prior art.

Thus, the invention provides a cyclopropanation process comprising the step of reacting an alkene compound having at least one carbon-carbon double bond (e.g. the alkene reactant) with at least one dihaloalkane (e.g., CBM) in the presence of:
(i) particulate metal Zn;
(ii) catalytically effective amount of particulate metal Cu or salts thereof.
(iii) at least one haloalkylsilane; and
(iv) at least one solvent;
thereby producing a cyclopropane derivative of said alkene compound (e.g. the cyclopropane product).

The term "cyclopropanation" relates to a process wherein a cyclopropane ring is formed on an alkene compound reacted in said process by the addition of a methylene moiety to at least one carbon-carbon double bond of said compound.

The term "alkene compound having at least one carbon-carbon double bond" as an alkene reactant encompasses any compounds having one or more carbon-carbon double bonds, being straight, branched, cyclic (i.e. cycloalkene) or multicyclic compounds (either fused rings, spiro ring systems or rings connected via chemical bonds). When the alkene reactant comprises more than one double bond, said at least two double bonds may be conjugated or none-conjugated. Said reactant may also comprise any functional groups and other types of bonds (sigma, triple or other). In embodiments wherein said alkene is substituted by more than one functional group directly bonded to the carbon atoms of said at least one carbon-carbon double bond, said alkene may be of cis or trans configuration or (Z) or (E) configuration.

The above term further includes the term "unactivated alkene" which should be understood to encompass a compound comprising an alkenyl group wherein the alkenyl double bond is not substituted with an electron withdrawing group (such as a nitrile group, a carboxylate group, or other electron deficient groups well-known in the art) that can activate a double (or triple) bond as a dienophile to react with a diene in a typical cycloaddition reaction. An unactivated alkene used as a reactant in a cyclopropantion process of the invention comprises at least one electron-donating group (such as for example alkyl, alkylaryl, alkoxyalkyl, cycloalkyl, cycloalkylalkyl or other electron-donating groups such as are well known in the art).

The term "dihaloalkane" should be understood to encompass any straight or branched $C_1$-$C_{10}$ alkane having two halogen atoms substituted thereon. In some embodiments said halogens are each independently Cl and/or Br. In some other embodiments said dihaloalkane is a dihalo-$C_1$-$C_5$ alkane.

In some embodiments said at least one dihaloalkane is dibromomethane (DBM), chlorobromomethane (CBM) or a combination thereof. In certain embodiments, said at least one dihaloalkane is dibromomethane. In other embodiments, said at least one dihaloalkane is chlorobromomethane.

It was surprisingly found that the carbenoid generated during the process of the invention by said dihaloalkane is extremely reactive, providing instant cyclopropanation of unactivated alkene reactants (i.e. alkene that are less reactive toward the electrophilic carbenoid. Such alkenes are typically unsubstituted or substituted with alkyl groups, carbonyl groups and so forth).

When referring to "particulate metal Zn" (also referred to as "Zn dust") it should be understood to encompass metal Zn particles. In some embodiments, the particulate metal Zn has particle size less than 10 μm (e.g., between 5 and 8 μm).

In some embodiments, particulate Zn contains at least 97% zinc, and in some embodiments the Pb content in the particulate Zn is 20 ppm or less.

In some embodiments, when said alkene reactant comprises one carbon-carbon double bond, said particulate metal Zn is present in an amount of 1-10 molar equivalents (e.g., 1-8, 2-8, 2-5, and 3 equivalents) relative to said alkene reactant.

When referring to "catalytically effective amount of particulate metal Cu" it should be understood to encompass particles of metal Cu that are added in catalytic amount (i.e. in an amount that is significantly lower than the stoichiometric amounts of the reactants of the process of the invention). In some embodiments, the particulate Cu is a particulate Cu salt, such as for example particles of CuCl. In some embodiments, said metal Cu particulate is present in the amount of 0.1 to 1% (e.g., 0.5%) by weight of the particulate metal Zn. In other embodiments, the metal Cu particulate is present in the amount of 0.1-20% (e.g., 0.2-15%, 0.5-10%, and 1-5%) by mole of the alkene reactant.

In some embodiments, said particulate metal Cu has a particle size of less than 50 μm. The copper particle size can vary from 37 to 105 μm (400 to 140 mesh), the preferred particle size is 44 μm (325 mesh).

In some other embodiments, the process of the invention is performed with catalytically effective amount of particulate Cu salt. In some embodiments, said Cu salt is CuCl. In some embodiments, the amount of the catalytically effective amount of particulate Cu salt is about 2 wt % relative to the amount of particulate metal Zn.

Without being bound by theory, Cu may serve to activate the surface of the particulate Zn. See also Blanchard and Simmons, *J. Am. Chem. Soc.* 86(7), 1337-47, 1964. Cu salts also can act as catalysts for the carbene transfer from the organozinc reagent to the alkene. See Schuchardt, Nery, and Zuiani, *J. Braz. Chem. Soc.* 2(2), 61-65, 1991 and references cited therein.

The term "haloalkylsilane" refers to a $C_1$-$C_{10}$ alkylSiX (wherein X is a halogen atom such as Cl, Br, and I). In some embodiments, said haloalkylsilane is chlorotrialkyl silane, which can be chlorotrimethylsilane, chlorotriethylsilane, chlorotributylsilane, chlorotriisobutylsilane, chlorotrihexylsilane, or any combination thereof. Chlorotrimethylsilane is preferred.

In some embodiments, the haloalkylsilane is present at a level of 0.5-5% (e.g., 1-3% and 1.5%) by weight of the particulate metal Zn.

In some embodiments, said at least one solvent is an ether solvent. In further embodiments, at least one ether solvent is selected from diethyl ether, 1,2-dimethoxyethane (DME), methyl tert-butyl ether, (MTBE), tetrahydrofuran (THF), cyclopentyl methyl ether (CPME) and any combinations thereof. In yet further embodiments, said at least one solvent further comprises dichloromethane (DCM).

In some embodiments, the solvent is a mixture of cyclopentyl methyl ether and dichloromethane having a weight ratio of 1:5 to 10:1 (e.g., 1:2 to 2:1, and 1:1).

In some embodiments, the weight ratio of said alkene compound and said at least one solvent is 1:1 to 10:1, preferably 2:1 to 7:1, and more preferably 4:1.

In some embodiments, the cyclopropanation process is performed in a temperature of between 20° C. to 100° C. (e.g., 35° C. to 70° C. and 53° C. to 58° C.).

In some embodiments, the cyclopropanation process of the invention provides a yield of between 50% and 90%. In other embodiments, the cyclopropanation process of the invention provides a yield of 85-95%.

When reacting a compound such as 2-alkyl-4-(2,2,3-trimethylcyclopent-3-en-1-yl)but-2-en-1-ol, valencene or D-Limonene, which contains two double bonds, they are both cyclopropanated in one step with a high yield. According to prior art (Friedrich and Niyati-Shirkhodaee, *J. Org. Chem.*, 56(6), 2202, 1991), D-limonene (IX) was reported to undergo mono and di-cyclopropanation using DBM to give a product mixture consisting of 22% unchanged starting material, 37% exocyclic cyclopropane, 12% ring cyclopropane, and 29% desired dicyclopropanated product X. In comparison, when cyclopropanating D-Limonene under the conditions of the process of the present invention, D-limonene was completely converted to the di-cyclopropanated product in 63% yield.

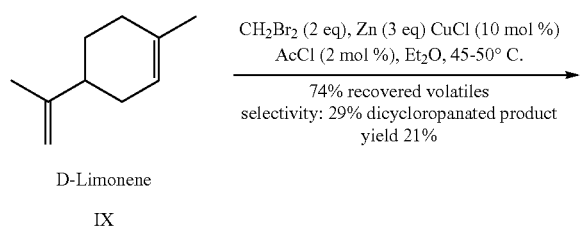

D-Limonene

IX

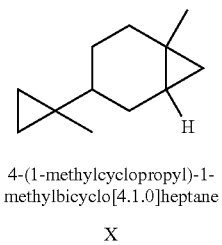

4-(1-methylcyclopropyl)-1-methylbicyclo[4.1.0]heptane

X

When THF or DME were used as the solvent, CBM selectively cyclopropanated the proximal allylic alcohol double bond of V to give VII in high yield. Alternatively, using half the equivalent amount of zinc in a mixture of CPME-DCM solvent and CBM as carbenoid source, the proximal double bond of V was rapidly titrated to afford VII in high yield.

When homoallylic alcohol such as (Z)-3-hexen-1-ol (XI, Leaf alcohol) was exposed to cyclopropanation process of the present invention (1R,2R)-2-ethyl-cyclopropaneethanol (XII) was formed in short time (3 hrs) and high yield (70%).

In comparison, Kiyota et al. reported the preparation of compound XII in 62% yield by reacting XI with expensive methylene iodide and highly pyrophoric diethyl zinc in boiling diethyl ether for 7 days. See *Flavour Fragr. J.* 17(3) 227-231 (2002).

Typically, compounds having a cyclopropane moiety, which are manufactured using a cyclopropanation process of the invention, are either precursors or ingredients with flavor and olfactory properties. Thus, the invention further provides a method of manufacturing a flavor or fragrance ingredient using the cyclopropanation processes described above with reduced costs and decreased environmental impacts.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

All publications cited herein are incorporated by reference in their entirety.

The invention is described in greater detail by the following non-limiting examples.

DETAILED DESCRIPTION

Example 1. [1-methyl-2-(1,2,2-trimethylbicyclo[3.1.0]hex-3-ylmethyl)cyclopropyl]methanol (VI)

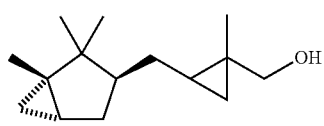

VI

To a reactor equipped with a reflux condenser was charged under nitrogen zinc dust (100 g, 1.48 mol), copper dust (0.5 g, 7.86 mmol), chlorotrimethylsilane (1.5 g, 0.0136 mol), CPME (100 g), and DCM (100 g). The mixture was stirred at 53-55° C. for 0.5 hours (hrs) followed by the addition of a mixture of (E)-2-methyl-4-(2,2,3-trimethylcyclopent-3-enyl)but-2-en-1-ol (V, 53 g, purity 92.5%, 0.25 mol) and CBM (165 g, purity 99%, 1.27 mol) during 2 hrs under gentle reflux. Ethylene is continuously evolved. After the addition was complete, the resultant reaction mixture was stirred at 58° C. for additional 1-1.5 hrs.

A solution of 50 wt % ammonium chloride in water (500 g) was cooled to 5° C. under stirring. After diluted with CPME (100 g), the reaction mixture was slowly added to the stirred aqueous ammonium chloride solution at 5° C. (exothermic). The temperature was allowed to rise during the addition up to 25° C. The organic phase was separated and washed with 10% aqueous sodium bicarbonate.

To the aqueous phase was added CPME (150 g) and stirred at room temperature for 15 minutes (min). The organic phase was collected and combined with the first organic phase obtained above. After distillation of solvent and the crude product at 190-220° C. and 0.1 mmHg in presence of 1 wt % sodium carbonate and 10% thermal oil, 43.6 g of VI was obtained, which had a purity of 82.5% (isomer 1-37.73%; isomer 2-44.73%). The weight yield is 89% (78% molar yield).

Example 2. [1-methyl-2-(1,2,2-trimethylbicyclo[3.1.0]hex-3-ylmethyl)cyclopropyl]methanol (VI)

To a reactor equipped with a reflux condenser was charged under nitrogen zinc dust (90 g), copper dust (1 g), chlorotrimethylsilane (1.5 g) and diethyl ether (200 g). The mixture was stirred at 45° C. for 0.5 hrs followed by the addition of a mixture of (E)-2-methyl-4-(2,2,3-trimethylcyclopent-3-enyl)but-2-en-1-ol (53 g, 92.5%, 0.25 mol) and CBM (206 g, 99%, 1.57 mol) during 2 hr under gentle reflux. After the addition is complete, the resultant mixture was stirred at 45° C. for additional 2 hr.

A solution of 50 wt % ammonium chloride in water (500 g) was prepared, cooled to 5° C. and kept under stirring. After diluted with diethyl ether (200 g), the reaction mixture was slowly added to the aqueous ammonium chloride solution at 5° C. (exothermic). The organic phase was separated and washed with an aqueous sodium bicarbonate solution containing sodium chloride. The organic phase was filtered. Diethyl ether was evaporated to obtain a crude product.

Subsequently, the crude product was distilled at 190-220° C. under 0.1 mmHg in the presence of 1 wt % sodium carbonate and 10% thermal oil to obtain 40 g of the product.

The purity was 82.5% (isomer 1-37.73%; isomer 2-44.73%). The weight yield was 80% (70% molar yield).

Example 3. [1-methyl-2-(1,2,2-trimethylbicyclo[3.1.0]hex-3-ylmethyl)cyclopropyl]methanol (VI)

The procedure described in Example 1 was followed except that CBM was replaced by DBM (275 g, 99%, 1.58 mol). The weight yield was 82% (71.8% molar yield).

Example 4. (1-methyl-2-(((R)-2,2,3-trimethylcyclopent-3-en-1yl)methyl)cyclopropyl)methanol (VII)

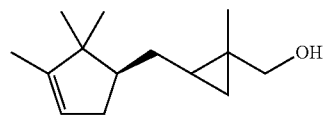

The procedure described in Example 1 was followed using the same amount of (E)-2-methyl-4-(2,2,3-trimethylcyclopent-3-enyl)but-2-en-1-ol (V) except that 85 g of CBM, 35 g of zinc dust, 0.25 g copper powder and 0.2 g of trimethylchlorosilane were used. The mixture of CBM and V was added during 1.5 hr at 60° C. Upon reaction completion, the reaction mixture was added slowly to a solution of ammonium chloride (75 g) dissolved in water (200 g). Flash distillation gave 45.5 g of a colorless viscous oil consisted of 74.8% of the monocyclopropanated product VII and 11.6% of VI. The weight yield of VII is 67.4% and that of VI is 10.45%.

(1-methyl-2-(((R)-2,2,3-trimethylcyclopent-3-en-1yl)methyl)cyclopropyl)-methanol (VII): 1H NR (500 MHz, CHLOROFORM-d): 5.17-5.30 (m, 1H), 3.24-3.40 (m, 2H), 2.27-2.44 (m, 1H), 1.62-1.95 (m, 3H), 1.53-1.62 (m, 3H), 1.20-1.52 (m, 2H), 1.14 (s, ~50% of 3H), 1.13 (s, ~50% of 3H), 0.98 (s, ~50% of 3H), 0.97 (s, ~50% of 3H), 0.74 (s, ~50% of 3H), 0.73 (s, ~50% of 3H), 0.38-0.68 (m, 2H), −0.18-0.11 (m, 1H). MS (DIP, EI): m/z 208 (M+).

Example 5. (4S,4aR)-4,4a-dimethyl-6-(1-methylcyclopropyl)decahydrocyclopropa[d]naphthalene

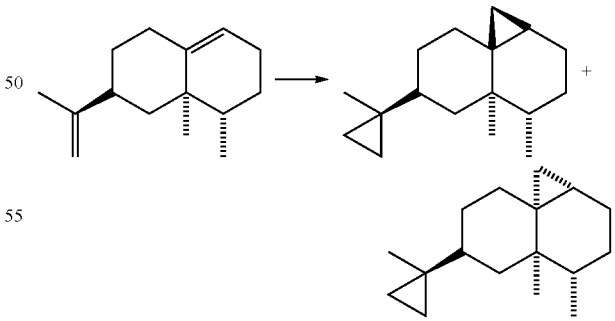

Valencene (15 g, 80%) was cyclopropanated according to the procedure described in Example 1 except using a different starting material (i.e., (3R,4aR,5S)-4a,5-dimethyl-3-(prop-1-en-2-yl)-1,2,3,4,4a,5,6,7-octahydronaphthalene) to give a mixture (15 g) of two isomers of 4,4a-dimethyl-6-(1-methylcyclopropyl)decahydrocyclopropa[d]naphthalene isomers in purity of 56%.

(4S,4aR)-4,4a-dimethyl-6-(1-methyl cyclopropyl)decahydrocyclopropa-[d]naphthalene: 1H NMR (400 MHz, CHLOROFORM-d): 0.94 (s, 3H), 0.90 (s, 3H), 0.85 (d, J=7.3 Hz, 3H), 0.10-2.43 (m, 19H). MS (DIP, EI): m/z 232 (M+).

Example 6. 5-isopropylspiro[bicyclo[3.1.0]hexane-2,1'-cyclopropane

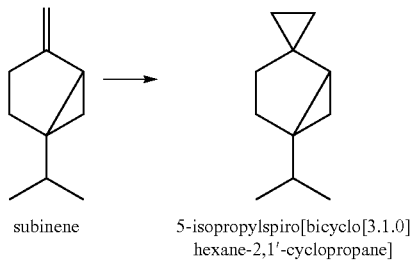

subinene       5-isopropylspiro[bicyclo[3.1.0]
               hexane-2,1'-cyclopropane]

Sabinene (25 g, two isomers at 74/26 ratio, minor isomer α-thujone) was cyclopropanated according to the procedure described in Example 1. There was complete conversion to give 29 g of product containing two isomers at 60/20 ratio.

The major isomer was identified as 5-isopropylspiro[bicyclo[3.1.0]hexane-2,1'-cyclopropane. 1H NMR (400 MHz, CHLOROFORM-d): 1.78-1.93 (m, 1H), 1.35-1.70 (m, 4H), 1.03-1.14 (m, 1H), 0.99 (d, J=6.8 Hz, 3H), 0.90 (d, J=6.9 Hz, 3H), 0.22-0.63 (m, 6H). MS (DIP, EI): m/z 150 (M+).

Sabinene was reported to undergo cyclopropanation by dihalocarbene followed by dehalogenation with Na/liquid ammonia. See Graefe, Lam and Muehlstaedt, *Zeitschrift fuer Chemie* 11(8), 304, 1971).

Example 7. 4-(1-methylcyclopropyl)-1-methylbicyclo[4.1.0]heptane (X)

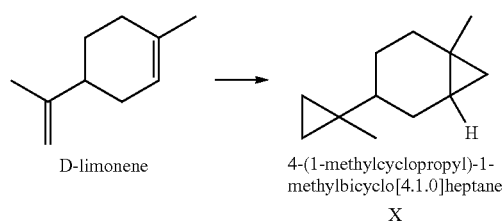

D-limonene       4-(1-methylcyclopropyl)-1-
                 methylbicyclo[4.1.0]heptane
                 X D-Limonene (38 g, 98% purity) was cyclopropanated following the procedure of Example 1. The starting material was completely converted to give 44 g of X of 65% purity. According to prior art (Friedrich and Niyati-Shirkhodaee, *J. Org. Chem.*, 56(6), 2202, 1991) the yield of the dicyclopropanated product was reported as 29%.

4-(1-methylcyclopropyl)-1-methylbicyclo[4.1.0]heptane (X): 1H NMR (400 MHz, CHLOROFORM-d): 0.63-2.06 (m, 8H), 1.05 (s, ~50% of 3H), 1.04 (s, ~50% of 3H), 0.90 (s, ~50% of 3H), 0.85 (s, ~50% of 3H), 0.04-0.55 (m, 6H). MS (DIP, EI): m/z 164 (M+).

Example 8. 3-methyl-Bicyclo[13.1.0]hexadecan-(4/5)-one

3-Methylcyclopentadec-(4/5)-ene-1-one (25 g, purity 95%), a mixture of 4 isomers with the major isomer as Z-3-methylcyclopentadec-5-ene-1-one, was cyclopropanated according to the procedure described in Example 1. The starting material was completely converted to 25 g of cyclopropanated isomers having a purity of 60%.

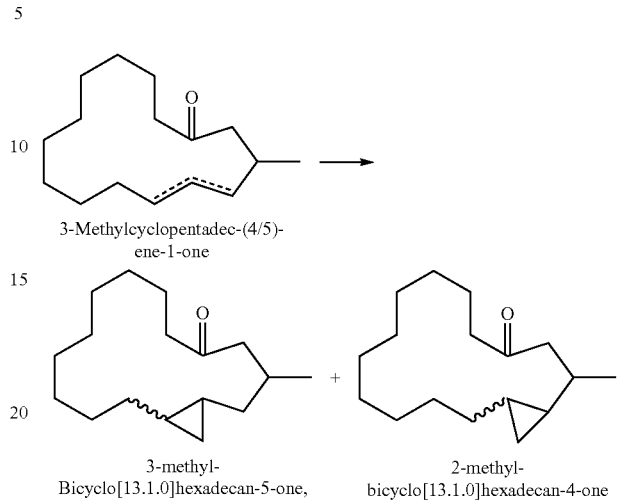

3-Methylcyclopentadec-(4/5)-
ene-1-one 3-methyl-                        2-methyl-
Bicyclo[13.1.0]hexadecan-5-one,  bicyclo[13.1.0]hexadecan-4-one The major isomer is 3-methyl-Bicyclo[13.1.0]hexadecan-5-one: 1H NMR (500 MHz, CHLOROFORM-d): 0.49-2.61 (m, 26H), 1.04 (d, J=6.6 Hz, 3H), −0.29-0.16 (m, 1H). MS (DIP, EI): m/z 250 (M+).

As disclosed in U.S. Pat. No. 7,943,559 (2011), 3-methyl-Bicyclo[13.1.0]hexadecan-5-one was prepared by cyclopropanation of 3-Methylcyclopentadec-(5)-ene-1-one by CH$_2$I$_2$/Et$_2$Zn.

Example 9. (1R,2R)-2-ethyl-Cyclopropaneethanol (XII)

To a reactor equipped with a reflux condenser was charged under nitrogen zinc dust (35 g, 0.535 mol), copper dust (0.1 g, 1.57 mmol), chlorotrimethylsilane (0.2 g, 1.85 mmol), CPME (60 g), and DCM (60 g). The mixture was stirred at 50° C. for 0.5 hr followed by the addition of a mixture of (Z)-3-hexen-1-ol (XI, 25 g, 0.245 mole, 98% purity) and CBM (50 g, 99% purity) during 1.5 hr at 50° C. The resultant reaction mixture was stirred for additional 2 hr and then worked up following the procedure described in Example 1. Flash distillation gave 25 g of colorless oil containing 80% of (1R,2R)-2-ethyl-cyclopropaneethanol (yield 70%).

1H NMR (500 MHz, CHLOROFORM-d) Shift: 3.73 (t, J=6.7 Hz, 2H), 1.67-1.81 (m, 1H), 1.31-1.48 (m, 3H), 1.23 (m, 1H), 0.99 (t, J=7.3 Hz, 3H), 0.56-0.83 (m, 3H), −0.29-0.18 (m, 1H). m/z 114 (M+).

What is claimed is:

1. A cyclopropanation process comprising the step of reacting an alkene compound having at least one carbon-carbon double bond with at least one dihaloalkane in the presence of (i) particulate metal Zn, (ii) catalytically effective amount of particulate metal Cu or a salt thereof, (iii) at least one haloalkylsilane, and (iv) at least one solvent; thereby producing a cyclopropane derivative of said compound, wherein the at least one solvent is a mixture of cyclopentyl methyl ether and dichloromethane having a ratio of between 1:5 to 10:1.

2. A cyclopropanation process according to claim 1, wherein said alkene compound has at least two carbon-carbon double bonds.

3. A cyclopropanation process according to claim 1, wherein said at least one dihaloalkane is dibromomethane, chlorobromomethane, or a combination thereof.

4. A cyclopropanation process according to claim 1, wherein said particulate metal Zn has particle size of less than 10 μm.

5. A cyclopropanation process according to claim 1, wherein said particulate metal Cu has particle size of less than 50 μm.

6. A cyclopropanation process according to claim 1, wherein said haloalkylsilane is chlorotrialkyl silane.

7. A cyclopropanation process according to claim 6, wherein said chlorotrialkyl silane is selected from the group consisting of chlorotrimethylsilane, chlorotriethyl silane, chlorotributylsilane, chlorotriisobutylsilane, chlorotrihexylsilane, and any combinations thereof.

8. A cyclopropanation process according to claim 1, wherein when said alkene compound comprises one double bond, said particulate metal Zn is added in an amount of 1-10 molar equivalents relative to said alkene compound.

9. A cyclopropanation process according to claim 1, wherein said particulate metal Cu is presented in an amount of 0.1 to 1 wt % of said particulate metal Zn.

10. A cyclopropanation process according to claim 1, having a yield of between about 50% to about 95%.

11. A method of manufacturing a flavor or fragrance ingredient, comprising the cyclopropanation process according to claim 1.

* * * * *